United States Patent [19]

Gergely

[11] Patent Number: 5,084,617
[45] Date of Patent: Jan. 28, 1992

[54] FLUORESCENCE SENSING APPARATUS FOR DETERMINING PRESENCE OF NATIVE HYDROCARBONS FROM DRILLING MUD

[75] Inventor: John S. Gergely, Ponca City, Okla.

[73] Assignee: Conoco Inc., Ponco City, Okla.

[21] Appl. No.: 526,074

[22] Filed: May 17, 1990

[51] Int. Cl.$^5$ .................. G01V 5/02; G01N 21/64
[52] U.S. Cl. ..................... 250/253; 250/227.23; 250/255; 250/256; 250/301; 250/461.1
[58] Field of Search ............... 250/253, 255, 256, 257, 250/268, 269, 372, 461.1, 301, 227.23

[56] References Cited

U.S. PATENT DOCUMENTS

| | | | |
|---|---|---|---|
| 2,591,737 | 4/1952 | Souther, Jr. | 250/255 |
| 4,149,805 | 4/1979 | Chew, III | 250/255 |
| 4,266,878 | 5/1981 | Auer | 356/419 |
| 4,609,821 | 9/1986 | Summers | 250/255 |
| 4,616,133 | 10/1986 | Senftle | 250/253 |
| 4,652,143 | 3/1987 | Wickersheim et al. | 374/161 |
| 4,662,749 | 5/1987 | Hatton et al. | 356/336 |
| 4,672,218 | 6/1987 | Chrisman et al. | 250/574 |
| 4,686,372 | 8/1987 | Satoru et al. | 250/461.2 |
| 4,692,611 | 9/1987 | Hoogenboom | 250/227 |
| 4,707,134 | 11/1987 | McLachlan et al. | 356/342 |
| 4,708,494 | 11/1987 | Kleinerman | 374/161 |
| 4,945,249 | 7/1990 | Grant et al. | 250/461.1 |
| 4,999,504 | 3/1991 | Braunuch et al. | 250/484.1 |

FOREIGN PATENT DOCUMENTS

| | | | |
|---|---|---|---|
| 1140011 | 2/1985 | U.S.S.R. | 250/301 |
| 8202573 | 8/1982 | World Int. Prop. O. | 250/255 |
| 8502015 | 5/1985 | World Int. Prop. O. | 250/255 |

OTHER PUBLICATIONS

Raymond M. Measures, Wayne R. Houston and David G. Stephenson, "Analyzing Fluorescence Decay", Laser Focus (Nov. 1974), pp. 49–52.

Primary Examiner—Constantine Hannaher

[57] ABSTRACT

A monitoring device for determining presence of native hydrocarbons downward along a drilled borehole by analyzing upcoming drilling mud returning to the reserve pit. The device includes a short pulse laser of selected output wavelength disposed at a remote location to couple output light into a fiber optic cable that leads to a position at the reserve pit viewing the returning drill mud. The device employs optical coupling to project any hydrocarbon fluorescence light for return along the fiber optic cable to the remote position for reflection through a monochromator, and the fluorescence light is processed through a photomultiplier tube and data acquisition system to derive charcteristic decay lifetime signatures to distinguish between native hydrocarbons and any lighter oils contained in the drilling mud.

11 Claims, 1 Drawing Sheet

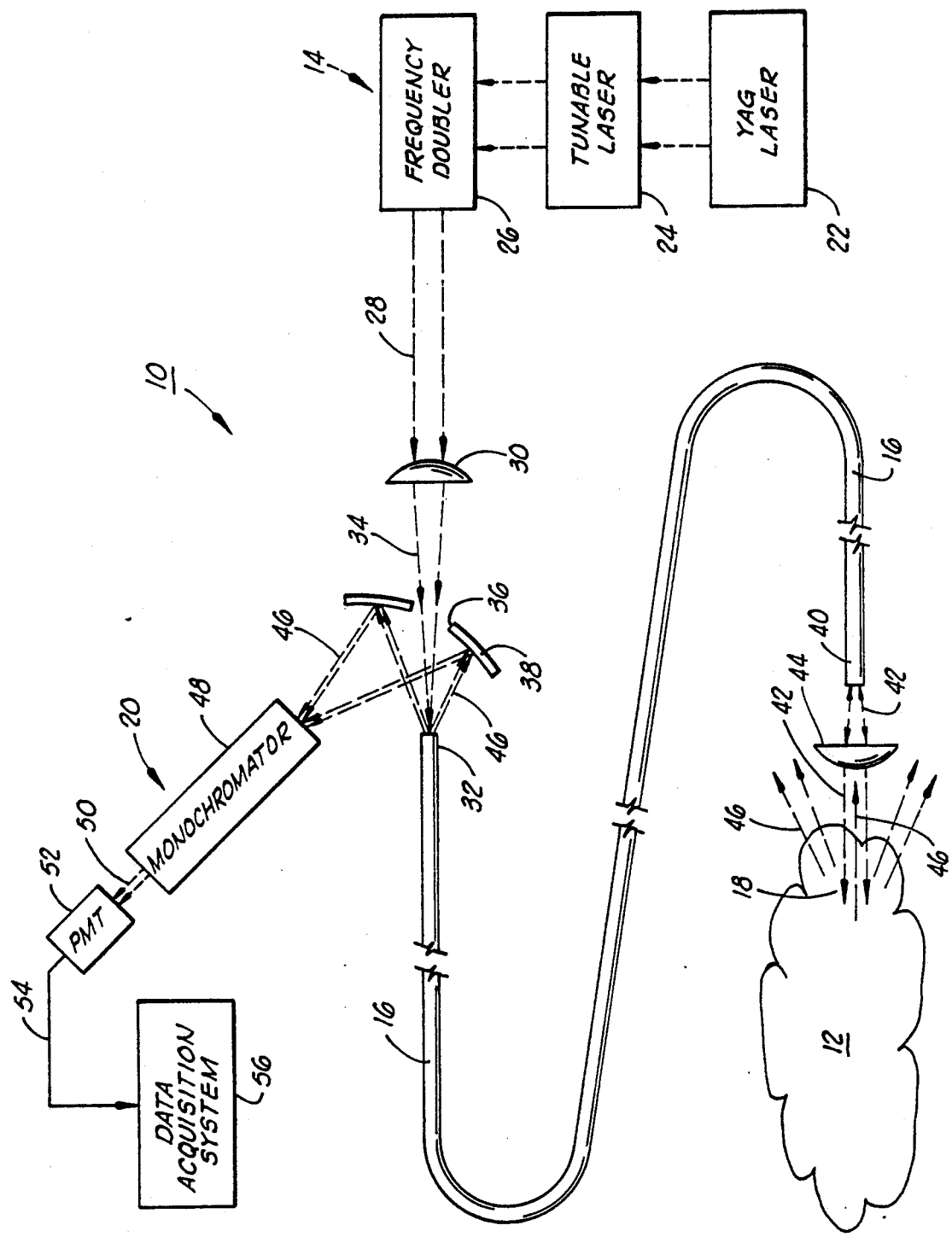

FLUORESCENCE SENSING APPARATUS FOR DETERMINING PRESENCE OF NATIVE HYDROCARBONS FROM DRILLING MUD

BACKGROUND OF THE INVENTION

1. Field of the Invention

The present invention relates to apparatus for remote sensing of drilling mud oil content to detect the presence of native hydrocarbons encountered downhole while also distinguishing from any oils that may be present in oil-base drilling muds.

2. Prior Art

There are presently a number of differing methods that rely upon fluorescence induced by ultraviolet light for indicating the presence of hydrocarbons. U.S. Pat. No. 2,591,737 is representative of an early form of drilling mud monitoring device that tests for crude oil presence by detecting characteristic fluorescence. This method employs steam distillation prior to treatment that enables visual inspection and identification of any oils present in the sample. U.S. Patents No. 4,692,611; 4,672,218; and 4,662,749 are illustrative of the use of fiber optic cable in remote sensing applications. Finally, U.S. Pat. No. 4,609,821 provides a method for testing for the presence of native hydrocarbons from a wellbore by testing a drilling mud sample for ultraviolet fluorescence response. This patent teaches the extraction and preparation of a test sample from a drill cutting present in the drilling mud flow. The prepared sample is then irradiated with ultraviolet light and synchronous excitation/emission relative intensity data is generated to give an indication.

SUMMARY OF THE INVENTION

The present invention employs time-resolved spectroscopy to derive decay lifetimes for fluorescence emissions from various oils, including native hydrocarbons. A remote light source in the form of a laser directs pulsed light of selected frequency into an extended fiber optic cable which leads from the remote position to a point adjacent the mud pit. Laser light output from the fiber cable is focused at the point where upcoming drilling mud circulates into the reserve pit, and any fluorescence at that point is radiated back through the fiber optic cable to the remote position whereupon the returning light emissions are separated by a spherical mirror and focused on a monochromator The monochromator provides output light of the selected wavelength onto a photomultiplier tube which, in turn, generates an electrical signal for input to a data acquisition system that classifies emission decay lifetimes and identifies native hydrocarbons versus any oils present in the drilling mud.

Therefore, it is an object of the present invention to provide a remote sensing apparatus for rapidly determining presence of a native hydrocarbon in drilling mud.

It is also an object of the invention to derive an indication of drilling success in rapid manner without necessitating expensive and time-consuming coring and other lost drilling time procedures.

It is yet another object of the present invention to provide a native hydrocarbon detector that is operable to examine and identify in the presence of either water-base or oil-base drilling muds.

Finally, it is an object of the present invention to provide apparatus for deriving time-resolved fluorescence data from a remote position that indicates hydrocarbon content of the drilling mud as it returns to the reserve pit.

Other objects and advantages of the invention will be evident from the following detailed description when read in conjunction with the accompanying drawing which illustrates the invention.

BRIEF DESCRIPTION OF THE DRAWING

The single drawing figure is a block diagram of the remote sensing apparatus.

DETAILED DESCRIPTION OF THE INVENTION

Heretofore, conventional drilling practice sought through various technologies to determine whether or not their drilling efforts were being successful. Thus, when the drill string extended down to estimated hydrocarbon bearing levels, it was one practice to withdraw the entire drill string from the borehole and thereafter to run a core test at the particular depth. That is, a coring apparatus was run down the borehole and operated to core a sample of material from the bottom of the hole for subsequent analysis. This was a very time consuming procedure and quite costly when considering additional labor and drilling time delays. It is also a practice to collect samples of rock cuttings brought up from the vicinity of the drill bit by the circulating drilling mud flow and to examine visually the cuttings in the presence of ultraviolet light. Since the aromatic components of native hydrocarbons fluoresced strongly under ultraviolet light it was possible for the skilled observer to read fluorescence indications and give a reasonably good estimate as to the presence of native hydrocarbons, this indicating that the target stratum of the drilling effort had been reached. Usually, upon getting a positive observation result, the drill string was withdrawn and then the borehole was cored to confirm the result.

These prior procedures were satisfactory when oil well drilling used conventional water-based drilling muds; however, such drilling muds are now being replaced in many applications by oil-based drilling muds. The oil-based drilling muds have many advantages such as prevention of hydration of shales, high temperature stability, excellent lubrication properties, etc. As deeper and more problematic formations are being investigated, the oil-base muds become increasingly important in exploration drilling, and certain environmental guidelines have necessitated the development of low toxicity oil-base muds, e.g., as formulated with low aromatic base oils, to replace diesel oil-based drilling muds. This is especially desirable to prevent toxic discharges to the marine environment from offshore drilling rigs.

With increasing use of diesel oil-base muds and low toxicity oil-base muds, difficulties arise in reliably testing for hydrocarbon ultraviolet light responses using the prior existing techniques. The reason for this is that the oil base of the drilling mud also contains aromatic components that fluoresce under ultraviolet and visible spectral regions and may be in confusion with native hydrocarbon indications. Under downhole conditions, mud filtrate to some extent invades the rock matrix, and its presence confuses the detection of native hydrocarbons by the conventional visual observation method.

The mixture of aromatic compounds contained in native hydrocarbons and drilling muds is complex, and contains fluorescing species in both the ultraviolet and visible parts of the spectrum. It is not unlikely that scattered and re-emitted light, which would be typically emitted in the ultraviolet at appropriate dilutions, may also be observed visually. Thus, while it may be possible for an observer to distinguish between certain fluorescences due to the presence of oil base drilling mud alone, and fluorescence due to a combination of oil-base and native hydrocarbons, it is a highly unsatisfactory test that may lead to false judgements as to the presence of native hydrocarbons. Here again, the overall drilling effort is set back and there is a considerable loss in drilling time while further attempts are made to confirm target depth of the borehole.

Referring to the drawing, a remote sensing apparatus 10 is used to provide ultraviolet to visible illumination of a portion of drilling mud 12 in order to determine presence of native hydrocarbons. A light source 14 is located at a remote location such as the rig floor doghouse or an equipment trailer whereupon it functions through an fiber optic cable 16 leading out to the rig reserve pit for irradiation of the drilling mud at a location 18 where the mud enters the reserve pit 12 as it is upcoming from the wellbore. In other words, it is drilling mud which is a designated time removed from presence at the borehole bottom. This travel time can be readily estimated so that a fluorescence test should coincide with bottom hole material from a designated depth or substratum. Spectral emission or fluorescence from mud location 18 is then conducted back through the fiber optic cable 16 for processing in the data analysis equipment 20.

A short pulse laser system is used that consists of a mode-locked, frequency-doubled YAG laser 22 that pumps a tunable, cavity-dumped, dye laser 24. Output light from tunable laser 24 is then passed through a frequency doubler 26, e.g., a section of KDP crystal, and the frequency doubled light beam 28 is then directed through a lens 30 for focused input to a remote end 32 of fiber optic cable 16. The f number of the lens 30 should be greater than the f number of the remote end 32 of fiber optic cable 16 to insure that the converging light enters the cable. The short pulse light in beam 28 is preferably continuously tunable over a range of 270–700 nanometers with pulse widths from 1 to 10 picoseconds and pulse repetition rates from 1 to 76 megahertz. The output wavelengths of the laser system are tuned to the ultraviolet spectral region where the oils, and particularly the native hydrocarbons, absorb best. The components of laser light source 14 can be acquired as a unit from Coherent, Inc. of Palo Alto, Calif. It should also be understood that there are commercially available equivalent laser devices that provide the requisite short pulse light within the desired frequency range.

The focused short pulse light 34 is matched for input at remote end 32 of fiber optic cable 16 after it passes through a central opening 36 in a spherical directional coupler 38, and light 42 at cable output end 40 is projected through a collimator lens 44 onto the mud location 18 whereupon it is selectively absorbed to excite identifiable fluorescent emissions 46. A suitable fiber optic cable 16 is commercially available from Guided Wave, Inc. of Eldorado Hills, Calif., and the lens 30 is a Type O1LQP001 that is available from Melles Griot, Inc. of Irvine, Calif. Light leaving the fiber cable 16 is collimated by the lens 44, a type 01 LQP 155 also available from Melles Griot, Inc. In some situations, it may be advisable to use a small telescope for focusing light transmission between output end 40 of fiber optic cable 16 and the mud pit location 18.

The collimated light 42 strikes the circulating mud entering the mud pit at location 18 and the mud emits fluorescing light 46 which is picked up by lens 44 and coupled back into the output end 40 of fiber optic cable 16. The fluorescent light response is conducted along fiber optic cable 16 and the fluorescent light 46 leaving the fiber optic cable 16 (at remote end 32) leaves at a wider angle than the laser light 34 that originally entered the cable 16. The wider, diverging fluorescent light 46 strikes the spherical surface of directional coupler 38 and is focused onto the input slit of monochromator 48, a type HR-320 monochromator that is commercially available from Instruments SA, Inc. Output light 50 is then selectively directed from monochromator 48 onto a photomultiplier tube 52 that develops an electrical output signal on lead 54 to a data acquisition system 56. The photomultiplier tube 52 is a multi-channel plate type photomultiplier tube that functions to convert the fluorescence beam 50 into a time-resolved electrical signal that is digitized, stored, and displayed in the data acquisition system 56. The photomultiplier tube is a type R2809U-07 that is commercially available from Hamamatsu, Inc., and the data acquisition system is a Data 6000 using a 640 plug-in that is commercially available from Data Precision, Inc.

The entire system or sensing apparatus 10, except for fiber optic cable 16 and collimating lens 44 (or the equivalent telescope) can be housed in an equipment trailer or within the doghouse at the rig floor. The fiber optic cable 16 can then be strung along the ground leading to the mud pit containing drilling mud 12. The end of the fiber optic cable 16 in association with collimating lens 44 is then secured in a position directed at the circulating mud entering the pit or mud location 18.

In operation, the response output at data acquisition 56 is monitored in relation to drilling depths in the well borehole as they relate to expected pays or production strata along the particular earth profile The time-resolved fluorescence spectra of an oil will have a very sharp rise time followed by a decay or fluorescence lifetime that varies characteristically in accordance with the type or molecular structure of hydrocarbon. Thus, both the fluorescence decay time and the emission frequency are contributing factors in identifying the particular fluorescing oil product. As a general rule, the presence of diesel oil in a drilling mud will exhibit a very short fluorescence lifetime and they have shorter wavelength ranges of excitation. Native hydrocarbons will tend to separate visually from oil-based drilling mud additives due to their longer decay or fluorescing lifetimes, and such indications are readily discernible from the output display of data acquisition system 56 in relation to the range of diesel and low toxicity oil additives.

The foregoing discloses a novel form of native hydrocarbon detector that uses a fiber optic cable interconnect from a remote position to examine fluorescence properties of upcoming drilling mud from the boreholes. Using the short pulse laser system and multichannel plate photomultiplier, a fluorescence spectrum takes less than a fraction of a second to form for output on the data acquisition system; therefore, once a native or other hydrocarbon of interest has risen to the surface, and is viewable in the mud pit it provides an immediate indication for the monitoring entity.

It should be understood that photon counting and phase modulation techniques can be used as well as the direct detection of time-resolved fluorescence spectra. Also, a streak camera can take the place of the multi-channel plate photomultiplier tube and operate to produce spectra of fluorescence intensity versus time (time-resolved fluorescence spectra) versus fluorescence emission wavelength. Yet another dimension can be added by obtaining the spectrum just mentioned for different excitation wavelengths. The streak camera is fast and has the ability to formulate an output spectra in the manner of the multi-channel plate photomultiplier tube, i.e., only fractions of a second are required to derive output indication for each excitation wavelength.

Changes may be made in combination and arrangement of elements as heretofore set forth in the specification and shown in the drawing; it being understood that changes may be made in the embodiments disclosed without departing from the spirit and scope of the invention as defined in the following claims.

The embodiments of the invention in which an exclusive property or privilege is claimed are as follows:

I claim:

1. Apparatus for remote sensing of drilling mud to determine the presence of native hydrocarbons in a well borehole, comprising:
    an ultraviolet to visible light source located at a position remote from said drilling mud;
    a fiber optic cable, having first and second ends with said first end positioned to receive ultraviolet to visible light input from said light source, and said second end being disposed adjacent the drilling mud returning from the borehole;
    light directive means for focusing ultraviolet to visible light from the cable second end onto the drilling mud and directing any fluorescence emission light into the cable second end;
    a light selecting means for directing fluorescence emission light from the cable first end in a selective light beam;
    a monochromator for receiving the selective light beam and providing an output beam;
    a photomultiplier means for receiving the output beam and producing a time-resolved electrical data signal; and
    data processing means including display for differentiating time-resolved data signals thereby to identify native hydrocarbons.

2. Apparatus as set forth in claim 1 wherein said ultraviolet to visible light source comprises:
    a laser producing pulsed output light in a selected UV to visible range.

3. Apparatus as set forth in claim 2 wherein said laser comprises:
    a first YAG laser pumping into a tunable dye laser that produces the output light.

4. Apparatus as set forth in claim 3 wherein: said output light from the dye laser is directed
    through a frequency doubling crystal to produce the source output light.

5. Apparatus as set forth in claim 1 which is further characterized to include:
    a lens coupling said ultraviolet to visible light input to the first end of the fiber optic cable.

6. Apparatus as set forth in claim 5 wherein: said light directive means is a collimating lens.

7. Apparatus as set forth in claim 1 wherein: said light directive means is a collimating lens.

8. Apparatus as set forth in claim 1 wherein said photomultiplier means comprises:
    a multi-channel plate photomultiplier that transforms the fluorescence signals into time-resolved electrical signals.

9. Apparatus as set forth in claim 1 wherein said light selecting means comprises:
    a directional coupler that allows beam passage of ultraviolet to visible light from the light source to the fiber optic cable first end, and spherically reflects fluorescence emission light from said cable first end to a focal point for input to said monochromator.

10. Apparatus as set forth in claim 9 wherein:
    the directional coupler is focused to place said focal point for the fluorescence emission light at the input slit of said monochromator.

11. Apparatus as set forth in claim 10 wherein said ultraviolet to visible light source comprises:
    a laser producing pulsed output light in a selected UV to visible range.

* * * * *